United States Patent [19]

Tanner

[11] Patent Number: 4,549,787
[45] Date of Patent: Oct. 29, 1985

[54] OPTICAL SHUTTER

[75] Inventor: Howard M. C. Tanner, Salt Lake City, Utah

[73] Assignee: HGM, Inc., Salt Lake City, Utah

[21] Appl. No.: 570,097

[22] Filed: Jan. 12, 1984

[51] Int. Cl.[4] .............................. G02B 5/20; G02B 7/00
[52] U.S. Cl. ........................................ 350/315; 350/318
[58] Field of Search .............. 350/315, 318, 319, 266, 350/269, 273

[56] References Cited

U.S. PATENT DOCUMENTS

| 431,692 | 7/1935 | Bar et al. | 350/315 |
| 3,299,771 | 1/1967 | Caulier et al. | 350/319 |
| 3,479,512 | 11/1969 | Weissenberg | 350/315 |
| 4,043,646 | 8/1977 | Heine et al. | 350/318 |

Primary Examiner—John K. Corbin
Assistant Examiner—Loha Ben
Attorney, Agent, or Firm—B. B. Olive

[57] ABSTRACT

A shutter mechanism for employment in an ophthalmic laser treatment system mounts between the binoculars and a slit lamp or operating microscope. The shutter mechanism provides a filter movable into the optical viewing path when the laser is under selected power during treatment to prevent damage to the operator's eyes from the laser beam and uncovers the viewing paths when said treatment site is being viewed in conjunction with laser beam alignment and similar pre-operational procedures.

7 Claims, 26 Drawing Figures

OPTICAL SHUTTER

DESCRIPTION

1. Technical Field

The invention relates generally to shutters for opening and closing light paths and more specifically to an optical shutter for use in a laser system associated with a slit lamp or an operating microscope for ophthalmic procedures to protect the user's eyes from harmful laser light.

2. Background Art

Laser systems associated with a slit lamp for ophthalmic procedures carried out in a doctor's office or associated with an operating microscope for ophthalmic procedures carried out in hospital surgery are known. As part of such procedures, the doctor typically views the operating site through binoculars while using a relatively low power laser aiming beam. At the time the laser is actually employed for the operating procedure at a higher power, it is necessary to protect the doctor's eyes from the laser beam. Therefore, various types of optical shutters have been devised for this purpose. Typically, the shutter is positioned by a solenoid drive mechanism which has the disadvantage of relatively slow speed and the further disadvantage of requiring substantial power relative to the power required by a motor drive as with the present invention. In other respects, the conventional optical shutters have employed plural lenses and mechanism for positioning such plural lenses between shielding and non-shielding positions.

With the mentioned prior art practices in mind, the object of the present invention is to provide an optical shutter mechanism employing a relatively fast motor drive, a self-latching mechaism and a single shutter lens for uncovering and covering dual light paths associated with binoculars and means for operating the lens with the motor so as to minimize the power required during the shutter operation. Other objects will become apparent as the description proceeds.

DESCRIPTION OF THE INVENTION

The invention is directed to providing a shutter mechanism comprising an assembly adapted to be installed between binoculars and either a slit lamp or operating microscope used in conjunction with a laser for ophthalmic procedures. Two light paths through the shutter mechanism correspond to the viewing paths of the binocular eye pieces. A single lens member is operatively associated with a motor-driven crank arm such that when the motor is energized, the lens can be quickly positioned to block both lights paths immediately prior to use of a high power laser beam and to assume a self-latching mode. Binoculars are secured on one side of the invention assembly and a slit lamp or operating microscope is secured on the opposite side of the invention assembly. The drive motor is powered through a foot switch such that when the foot switch is operated, the shutter moves into position to block both light paths and thereby protect the eyes of the operator, i.e., the doctor or surgeon performing the ophthalmic procedure. As the shutter rotates to its shielding position, a position sensitive switch is actuated which enables laser power to be applied to the operation site at a selected high level and for a brief interval of time. Release of the foot switch serves to reverse the direction of operation of the motor and to restore the shutter to its non-blocking position prior to which the laser power level will have been restored to a level that will not be harmful to the operator or patient.

BEST MODE FOR CARRYING OUT THE INVENTION

Figure 1:
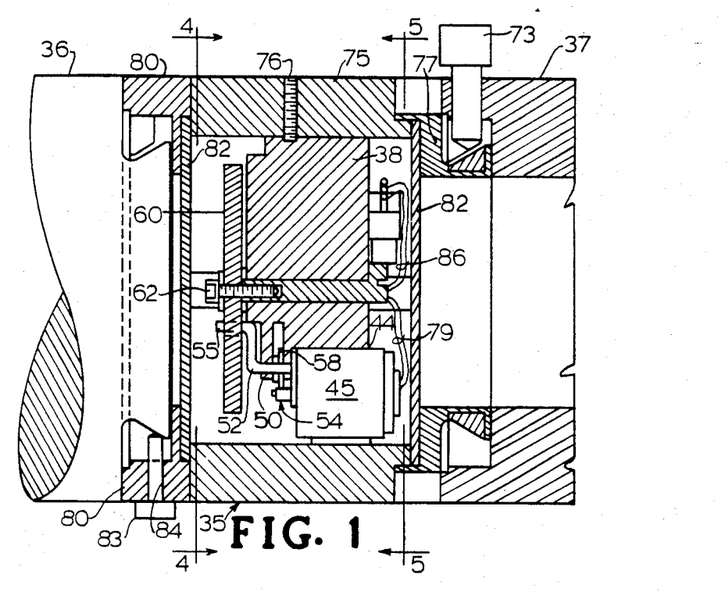
FIG. 1 is a cross section of the invention shutter mechanism assembly and illustrating how the slit lamp or operating microscope fitting and the binoculars are clamped to opposite ends of the invention assembly.
Figure 2:
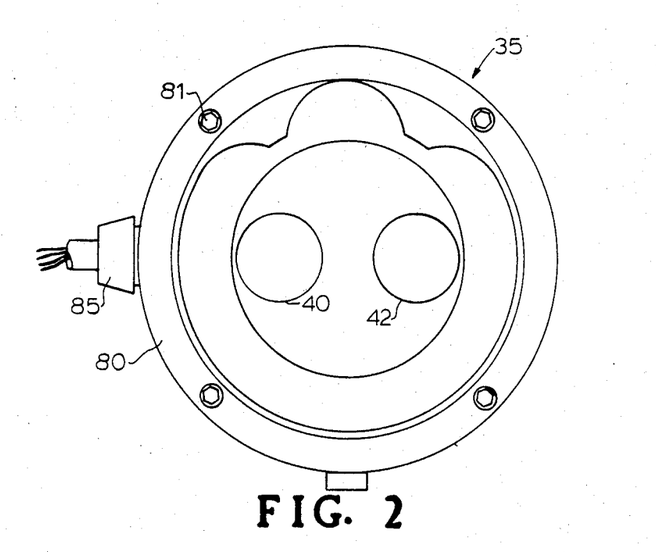
FIG. 2 is a left end view of the assembly of FIG. 1.

Referring initially to FIG. 1, the shutter mechanism 35 of the invention is adapted to be installed in an ophthalmic laser system between binoculars 36 and a slit lamp or operating microscope fitting 37 as indicated in FIG. 1. The description will first describe the electromechanical construction of the invention shutter mechanism 35 and will then discuss its operating features.

Figure 6:
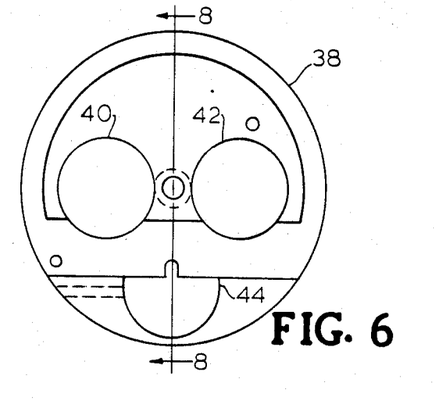
FIG. 6 is a left end view of the shutter core.
Figure 7:
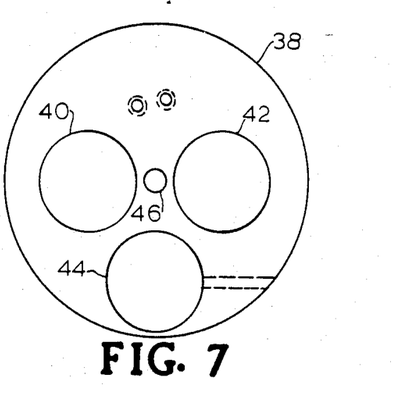
FIG. 7 is a right end view of the shutter core.
Figure 8:
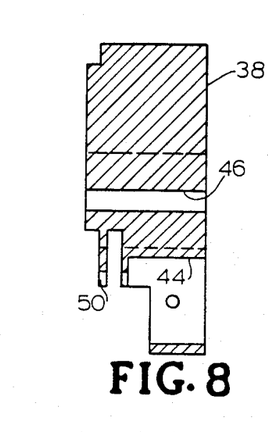
FIG. 8 is a section view taken along line 8—8 of FIG. 6.
Figure 9:
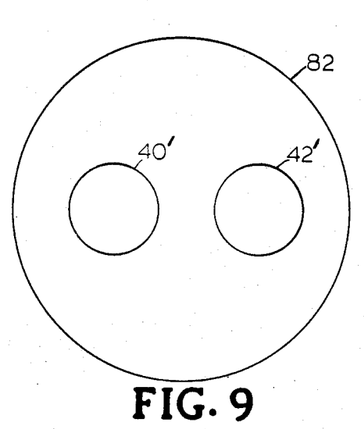
FIG. 9 is an end view of a core cover.
Figure 10:
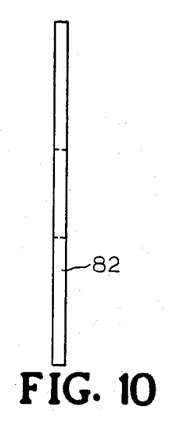
FIG. 10 is a side view of a core cover.

As seen in FIG. 1, the shutter mechanism 35 comprises the shutter core 38 formed of black coated aluminum and as best seen in FIGS. 6, 7 and 8 includes a pair of laterally-spaced, horizontally-oriented apertures or bores 40, 42 which align with the binocular sight paths, an aperture-recess formation 44 for mounting the filter drive motor 45 (FIGS. 1 and 4), a hole 46 between and on the horizontal centerline of holes 40, 42 for mounting the shutter mounting shaft taken along line 13—13 of FIG. 11 48 and a rib portion 50. Motor 45 drives the end 53 of filter crank 52 through gear 54 on the motor shaft and gear 58 on crank end 53. The outer crank end 55 slides in a slot 56 formed in the shutter filter 60. Filter 60 is formed of thin, e.g. 0.125 inch, amber-tinted, transparent "Plexiglas" sheet material. Filter 60 is in turn secured by bolt 62 on one end of mounting shaft 48 and is formed with outwardly-extending filter lens sections 65, 66 which can be brought into the binocular sight paths, i.e., to cover holes 40, 42, as in the dashed line position of FIG. 4 or in a position to uncover such light paths as in the solid line position of FIG. 4. Radially-oriented slot 56 is formed alongside section 66. Adjustable stops 70, 72 are utilized to respectively limit the counterclockwise and clockwise directions of travel of the shutter filter 60 as viewed in FIG. 4.

Core 38 mounts in the aluminum-formed shutter housing 75 which provides a hollow interior and wire entryway 74 and is secured by set screw 76. An aluminum-formed male shutter flange 77 retains a thin, metal plate core cover 82 with holes 40', 42' aligned with holes 40, 42. Flange 77 is secured by screws 78 to one side of housing 75 for receiving the previously-mentioned slit lamp or operating microscope fitting 37 utilizing thumb screw 73. An aluminum-formed female shutter flange 80 retains another core cover 82 and is secured by screw 81 to the opposite end of housing 75. The female shutter flange 80 is adapted to receive the binoculars 36 and secure such binoculars by means of a thumb screw 83 inserted in the threaded hole 84 (FIG. 1). Flanges 77 and 80 may, if desired, be formed integrally with respective core covers 82.

Figure 5:
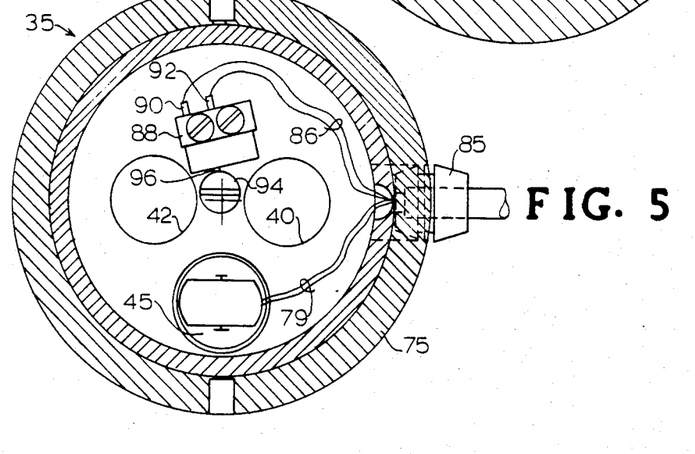
FIG. 5 is a section view taken along line 5—5 of FIG. 1.

Drive motor 45 comprises a microsize, reversible DC motor energized through a pair of leads 79 which in turn are fed from the shutter mechanism 35 through a grommet 85 (FIG. 5) which also receives another pair of leads 86 connected to a microswitch 88. Contacts 90, 92 are opened and closed by means of a cam 94 which contacts switch actuator 96 (FIG. 5). Cam 94 on the end of the shutter mounting shaft 48 engages switch actuator 96 whenever the shutter filter 60 is in the shielding position as indicated in dashed lines in FIG. 4. Thus, switch 88 is normally employed as a means to signal and allow the laser source to produce a laser pulse and to deenergize drive motor 45 through appropriate control circuitry when the filter shutter 60 is in the filtering position. Also, through appropriate controls the laser is then pulsed at selected power without danger to the operator's eyes.

Figures 3, 4:
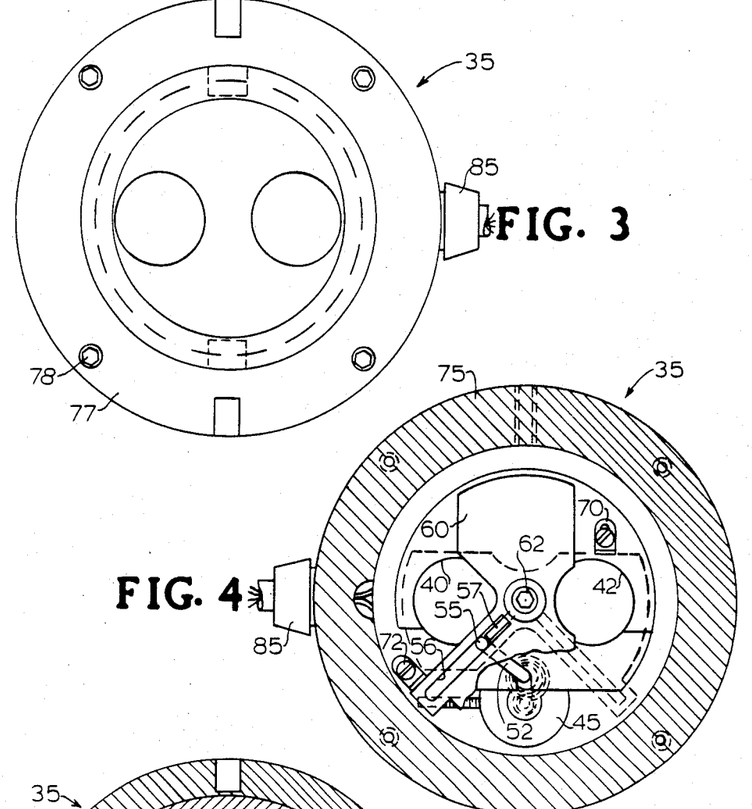
FIG. 3 is a right end view of the assembly of FIG. 1.
FIG. 4 is a section view taken along line 4—4 of FIG. 1.
Figure 26:
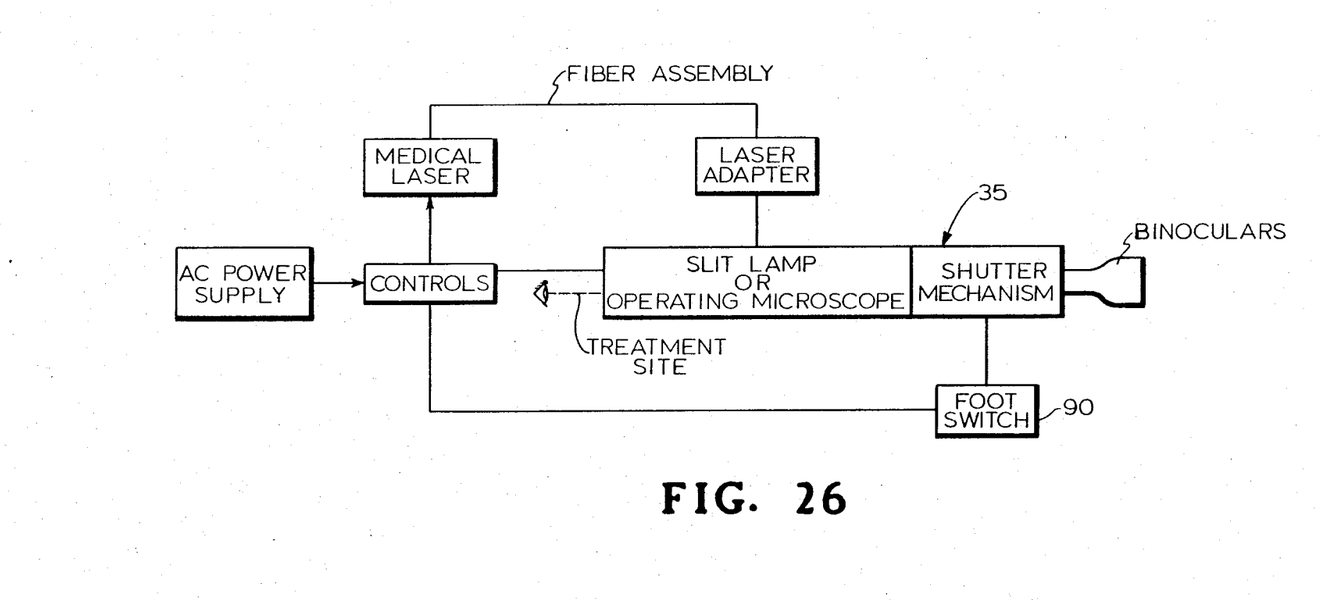
FIG. 26 is a simplified schematic diagram of a system incorporating the shutter mechanism of the invention.

In the general system diagram illustrated in FIG. 26, operation of foot switch 90 is coordinated with the application of the briefly pulsed laser beam under selected operating power such that when the foot switch 90 is depressed, a pulse of power is applied to drive motor 45 to move the shutter filter 60 to the closed or filtering position and when the operator removes his foot from the foot switch 90, a pulse of power is applied to drive motor 45 so as to cause the filter crank 52 to rotate the shutter filter 60 to the nonfiltering position as indicated in the solid line position of filter 60 in FIG. 4. Appropriate controls apply such power pulses and in correct polarity relation for the desired direction of rotation. The foot switch 90 as indicated in FIG. 26 is linked electrically to the laser source and thus the selected pulse of laser power can be applied after the usual preliminary aiming and aligning procedure has been accomplished. The adjustable stops 70, 72 limit the travel of shutter filter 60. A cylindrical rubber bumper 57 secured to filter 60 extends into slot 56 of shutter filter 60 to absorb any shock induced by crank overtravel. Also to be noted is that crank 52 and slot 56 are oriented operationally such that when filter crank 52 drives the shutter filter 60 into either the nonfiltering position as in solid lines in FIG. 4 or in the filtering position as in dashed lines in FIG. 4, the filter crank 52 assumes a self-latching position. By this is meant that when the shutter filter 60 is in either the nonfiltering or filtering position, it cannot be rotated from such position except by energizing drive motor 45 by a short power pulse of suitable duration and polarity for the appropriate direction of rotation to drive filter crank 52 accordingly.

Of particular significance is the relation of the filter crank 52 to the shutter filter 60. In this regard, slot 56 (FIG. 4) is oriented with respect to filter crank 52 such that when motor 45 is initially energized by a power pulse to move shutter filter 60 to the blocking position, indicated in dashed lines in FIG. 4, filter crank 52 can actually rotate and move approximately 15° to 20° before any load is transferred to drive motor 45. Thus, when a load is initially placed on motor 45, the motor is operating at near maximum power output and is thus at or near-peak efficiency. This allows the shutter filter to be moved to blocking position very rapidly, e.g., in 40 to 50 milliseconds and with minimum power requirement. In one embodiment an extremely small Micromo Series 1516 motor was employed with satisfactory results.

Since shutter filter 60 is of a single-piece, thin, plastic plate construction and includes slot 56, filter crank 52 can be connected directly to shutter filter 60 without intermediate linkage. Further, the described tinted, Plexiglas thin-plate filter construction eliminates the need for plural ground glass blocking lenses as in prior art devices and provides an extremely lightweight and easily rotated filtering lens.

What is claimed is:

1. A shutter mechanism for employment in a laser system between binoculars and a slit lamp or operating microscope, comprising:
    (a) an outer housing providing a hollow interior and a wiring entryway through the wall thereof;
    (b) an inner housing within said outer housing, said inner housing being formed with a pair of laterally-spaced, horizontally extending apertures alinged with optical sight paths of binoculars associated with said mechanism and located on a common horizontal centerline, a receptacle formation adapted for receiving a filter shutter drive motor and a shaft mounting hole passing through said inner housing and having its axis parallel to, located between, and aligned with said horizontal centerline;
    (c) a filter-mounting shaft rotatably mounted in said shaft mounting hole, said shaft having a cam formed on one end and the opposite end accessible and adapted for mounting another member thereon;
    (d) a filter member secured to said shaft opposite end and rotatable therewith, said filter member being formed as an integral thin transparent sheet with an appropriate filtering tint, having filtering sections extending outwardly from a central point about which said filter member rotates with said shaft and adapted when said filter member and shaft are rotated in one direction to cover said pair of apertures and when rotated in an opposite direction to uncover said pair of apertures and having a slot extending radially outward from said central point and alongside one of said sections;
(e) drive means including a drive motor mounted in said receptacle formation, a gear train driven by said motor and a crank arm driven by said gear train, with the outer end of said crank arm being mounted in said slot to drive said filter member;
(f) a first flange member mounted on one end of said outer housing for releasably receiving binoculars associated with said mechanism;
(g) a second flange member mounted on an opposite end of said housing for releasably receiving a slit lamp or operating microscope fitting associated with said mechanism;
(h) a switch having a contact positioned such that when said filter member and shaft rotate to cover said pair of apertures said cam engages said contact to actuate said switch and when said filter member and shaft rotate to uncover said pair of apertures said cam moves out of engagement with said contact to deactuate said switch; and
(i) operator means associated with said switch for energizing said motor to move said filter to cover said pair of apertures during time periods when operating and effecting treatment with a laser source associated with said mechanism and to uncover said pair of apertures at other times.

2. A shutter mechanism as claimed in claim 1 wherein said filter member slot and crank arm are oriented operationally to effect a self-latching mode when said filter member is moved to either the position in which said pair of apertures are uncovered or in which said pair of apertures are covered.

3. In a laser system having a laser source and means utilizing the laser beam from said source for treatment at a selected site on a human body, a shutter mechanism for employment in optical viewing paths associated with said treatment, comprising:
(a) housing structure providing a pair of apertures aligned with and forming part of a corresponding pair of optical viewing paths for viewing the treatment site;
(b) a drive mechanism mounted in said structure and including a bi-directional drive motor and a crank arm driven by said motor;
(c) a filter member rotatably mounted on said structure for movement between a first position in which said filter member covers said apertures and a second position in which said filter member uncovers said apertures, said filter member comprising a thin, transparent tinted sheet member having filtering sections extending outwardly from a central point about which said filter member rotates, said crank arm being mechanically linked to said filter member enabling said motor when appropriately energized to selectively drive said filter member to either of said positions; and
(d) wherein:

(i) said filter member includes a slot, said crank arm has an outer driven end slidable in said slot to mechanically link said filter member and crank arm; and
(ii) said crank arm and slot are oriented operationally to effect a self latching mode when said filter member is moved to either said position.

4. In a laser system as claimed in claim 3 including:
(a) a shaft centrally mounted in said structure, said filter member being secured to one end of said shaft for rotation about the axis of said shaft and said shaft having a cam formed at the opposite end thereof; and
(b) a switch mounted on said structure having a contact engageable with said cam when said filter member is moved to said first position to actuate a pair of contacts in said switch and being disengageable from said cam when said filter member is moved to said second position to deactuate said switch.

5. In a laser system as claimed in claim 3 including first and second flange members mounted on opposite ends of said structure for releasably receiving at one end binoculars and at the opposite end a slit lamp or operating microscope fitting associated with said shutter mechanism.

6. In a laser system as claimed in claim 3 wherein said crank arm is adapted to rotate at least slightly when changing positions before imposing the full load of said filter member on said drive motor.

7. In a laser system having a laser source and means for utilizing the laser beam from said source for treatment at a selected site on a human body, a shutter mechanism for employment in optical viewing paths associated with said treatment, comprising:
(a) housing structure providing a pair of apertures aligned with and forming part of a corresponding pair of optical viewing paths for viewing the treatment site;
(b) a drive mechanism mounted in said structure and including a bi-directional drive motor;
(c) a filter member rotatably mounted on said structure for movement between a first position in which said filter member covers said apertures and a second position in which said filter member uncovers said apertures, said filter member comprising a thin, transparent tinted sheet member having filtering sections extending outwardly from a central point about which said filter member rotates;
(d) drive means mechanically linking said filter member to said drive motor enabling said motor when appropriately energized to selectively drive said filter member to a self-latching mode in either of said positions; and
(e) switching means mounted on said structure and including actuating means associated with said filter member and operable when said filter member is moved to said first position to actuate a pair of contacts and when said filter member is moved to said second position to deactuate said contacts.

* * * * *

UNITED STATES PATENT AND TRADEMARK OFFICE
CERTIFICATE OF CORRECTION

PATENT NO. : 4,549,787

DATED : October 29, 1985

INVENTOR(S) : Howard M. C. Tanner

It is certified that error appears in the above—identified patent and that said Letters Patent is hereby corrected as shown below:

Column 1, line 53, correct "lights" to read --light--.

Figure 11:
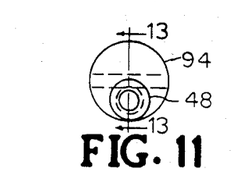
FIG. 11 is a left end view of the shutter mounting shaft.
Figure 12:
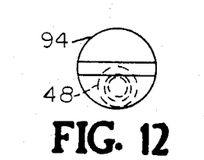
FIG. 12 is a right end view of the shutter mounting shaft.
Figure 13:
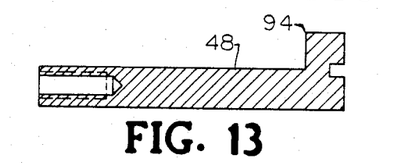
FIG. 13 is a cross section of the shutter mounting shaft.
Figures 14, 15:
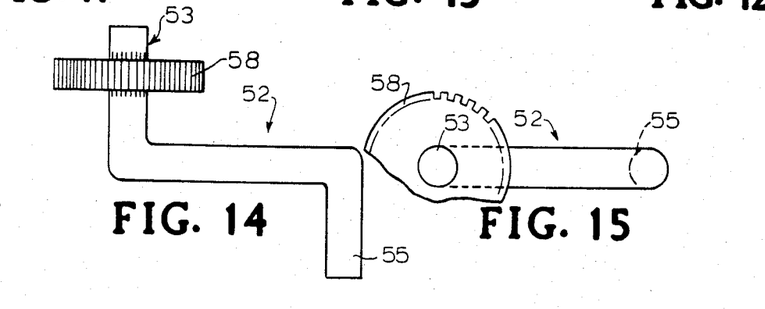
FIG. 14 is a side view of the filter crank.
FIG. 15 is an end view of the filter crank.
Figures 16, 17:
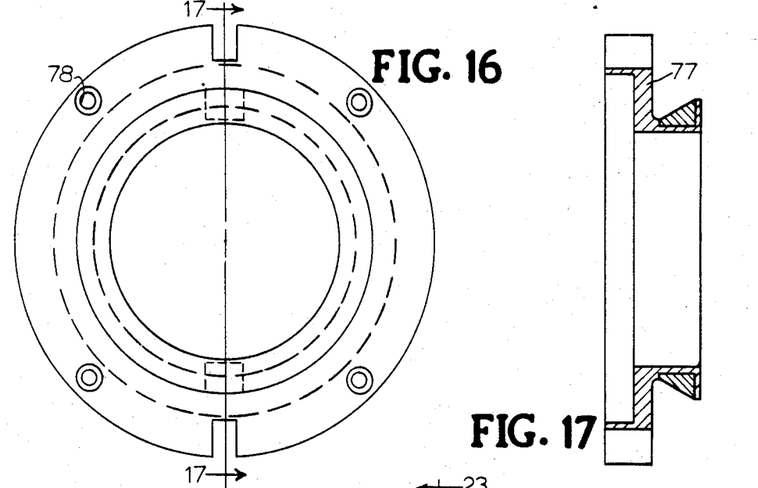
FIG. 16 is an outer end view of the male shutter flange which is adapted to fit a slit lamp or operating microscope fitting.
FIG. 17 is a section view taken along line 17—17 of FIG. 16 of the male shutter flange.
Figure 18:
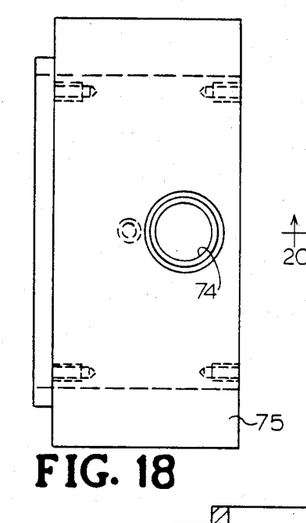
FIG. 18 is a side view of the shutter housing.
Figure 19:
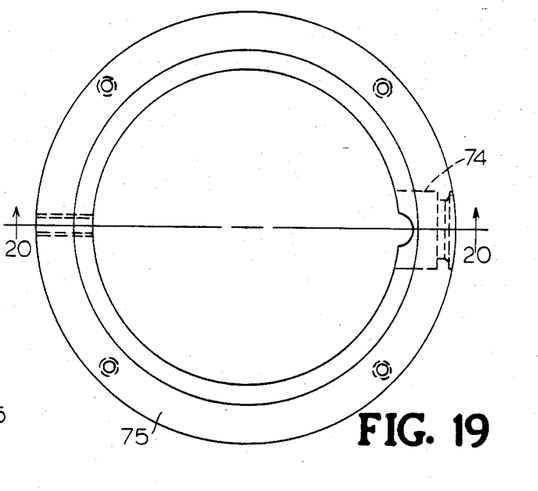
FIG. 19 is a left end view of the shutter housing.
Figure 20:
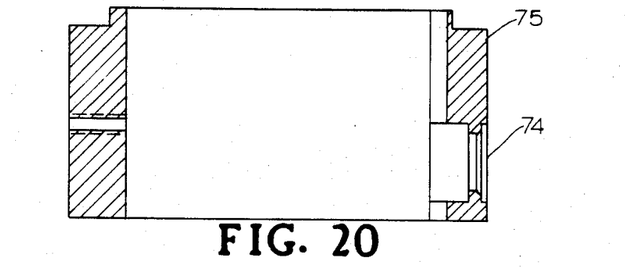
FIG. 20 is a section view taken along line 20—20 of FIG. 19.
Figure 21:
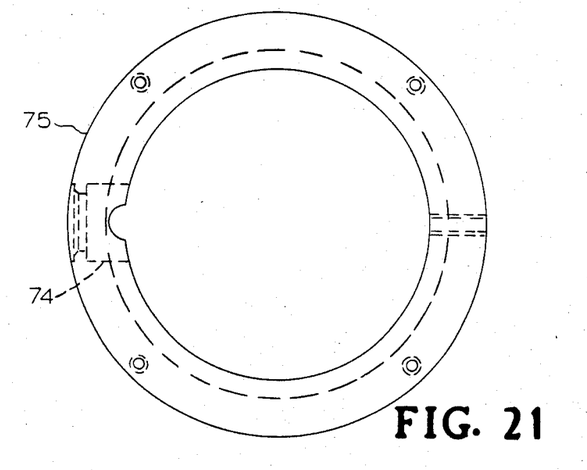
FIG. 21 is a right end view of the shutter housing.
Figures 22, 23, 24, 25:
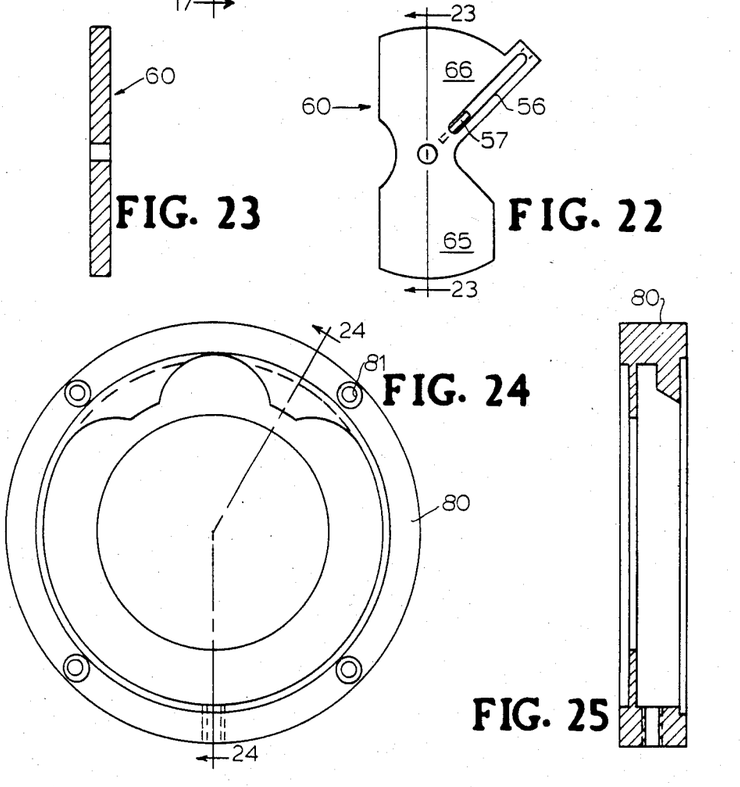
FIG. 22 is a side view of the shutter filter.
FIG. 23 is a section view taken along line 23—23 of FIG. 22.
FIG. 24 is an outer end view of the female shutter flange which is adapted to accept the binoculars.
FIG. 25 is a section view taken along line 24—24 of FIG. 24.

Column 2, line 27, insert --taken along line 13-13 of Fig. 11-- after "shaft".

Column 2, line 68, through column 3, line 1, delete "taken along line 13-13 of Fig. 11".

Signed and Sealed this

Twenty-first Day of January 1986

[SEAL]

Attest:

DONALD J. QUIGG

Attesting Officer     Commissioner of Patents and Trademarks